United States Patent [19]

Schuur et al.

[11] Patent Number: 4,795,260

[45] Date of Patent: Jan. 3, 1989

[54] APPARATUS FOR LOCATING AND TESTING AREAS OF INTEREST ON A WORKPIECE

[75] Inventors: John Schuur, San Jose; David L. Willenborg, Dublin; Michael W. Taylor, Oakland; Allan Rosencwaig, Danville, all of Calif.

[73] Assignee: Therma-Wave, Inc., Fremont, Calif.

[21] Appl. No.: 50,911

[22] Filed: May 15, 1987

[51] Int. Cl.$^4$ .............................................. G01N 21/00
[52] U.S. Cl. ...................................... 356/400; 356/432
[58] Field of Search .................... 356/432 T, 400, 401, 356/398, 375

[56] References Cited

U.S. PATENT DOCUMENTS

| | | | |
|---|---|---|---|
| 3,977,789 | 8/1976 | Hunter et al. | 356/120 |
| 4,406,545 | 9/1983 | Montone et al. | 356/380 |
| 4,544,889 | 10/1985 | Hendricks et al. | 356/375 |
| 4,597,669 | 7/1986 | Terasawa et al. | 356/401 |
| 4,636,088 | 1/1987 | Rosencwaig et al. | 356/432 |

OTHER PUBLICATIONS

"Thermal and plasma wave depth profiling in silicon", Jon Opsal and Allan Rosencwaig *Appl. Phys. Lett.* 47 (5) 1 Sep. 1985 p. 498.

*Primary Examiner*—Richard A. Rosenberger
*Attorney, Agent, or Firm*—Limbach, Limbach & Sutton

[57] ABSTRACT

The subject invention relates to a method and apparatus for identifying and testing the location of areas of interest on a workpiece and specifically, unmasked areas on a semiconductor wafer. In the subject method, the surface of the wafer is scanned with a search beam of radiation. The power of the reflected search beam will be a function of the optical reflectivity of the surface of the sample. Since the optical reflectivity of the unmasked areas are different from the masked areas, the power measurement of the reflected search beam can be used to identify the location of areas to be measured. In the preferred testing procedure, an intensity modulated pump beam is used to periodically excite a region in the identified unmasked area. A probe beam is then directed within the periodically excited region and the periodic changes in the power of the reflected probe beam, induced by the pump beam, are measured to evaluate ion dopant concentrations or the effects of processing steps, such as etching, on the surface of the wafer.

23 Claims, 3 Drawing Sheets

APPARATUS FOR LOCATING AND TESTING AREAS OF INTEREST ON A WORKPIECE

TECHNICAL FIELD

The subject invention relates to a method and apparatus for identifying areas of interest on a workpiece for subsequent testing. Optical reflectivity characteristics at the surface of the workpiece are used to locate areas of interest which then can be probed for information concerning the workpiece. The invention is particularly suited for identifying unmasked areas on a semiconductor wafer and for testing the wafer for ion dopant concentrations or the effects of various processing steps.

BACKGROUND OF THE INVENTION

In a prior art, significant developments have been made for non-destructively testing surface and near surface conditions on samples. For example, the assignee of the subject invention has developed a number of special techniques for measuring surface and subsurface conditions in the sample. In U.S. Pat. No. 4,521,118, issued on June 4, 1985, and U.S. Pat. No. 4,522,510, issued on June 11, 1985, a technique is disclosed for detecting thermal waves using a laser beam deflection system. The detected thermal waves are used to evaluate thermal parameters in the sample.

In U.S. Pat. No. 4,579,463, issued on April 1, 1986, a second technique is disclosed for detecting thermal waves. This technique relies on the measurement of periodic changes in optical reflectivity of the sample as it is periodically heated by a modulated pump source. The apparatus for performing this technique can also be used to evaluate semiconductor samples as disclosed in U.S. Pat. No. 4,636,088. In a semiconductor, the modulated pump source functions to generate plasma waves in the sample which have a direct effect on its optical reflectivity. This technique can provide very useful information on ion-dopant concentrations and about the etching steps. The generation and detection of plasma waves is described in U.S. patent application Ser. No. 707,485, filed on Mar. 1, 1985, assigned to the same assignee as the subject invention. The physics underlying the device disclosed in the latter patent application is described in "Thermal and Plasma Wave Depth Profiling in Silicon" *Applied Physics Letters,* Opsal and Rosencwaig, Volume 47(5), page 498, Sept. 1, 1985. All of the above patents and the latter application and article are hereby incorporated herein by reference.

As will be discussed below, the apparatus of the subject invention utilizes a beam of radiation to search out and locate areas of interest on a workpiece. Each of the above described techniques for evaluating samples also employs at least one beam of radiation. For this reason, the measurement devices developed by the assignee herein are particularly suited to form a portion of the subject invention since much of the existing hardware in the prior art devices can be modified to sense and locate areas of interest on a workpiece.

One of the biggest difficulties facing the semiconductor industry is poor fabrication yields. The principal reason for such low yields is the lack of a totally clean environment. Contamination can most often be traced to handling of the wafers by human personnel. Therefore, significant effort has been expended in trying to develop machinery which will automate the manufacturing process.

Much of the automated equipment in use today consists of handling devices used to move semiconductors from one area to another. There also exist relatively sophisticated inspection systems which include complex machine imaging systems. The imaging systems are used to locate and inspect specific regions on the semiconductor wafer. As is well-known, semiconductors are manufactured by a plurality of masking steps. Areas within the mask are etched and then treated through subsequent process steps. Some inspection equipment has been designed to determine if the proper etch pattern has been laid down on the semiconductor. In order to achieve this result, a highly sophisticated pattern recognition system must be used. One such pattern recognition system is disclosed in U.S. Pat. No. 4,597,669, issued July 1, 1986 to Terasawa. These pattern recognition devices require high speed microprocessors and large memory storage capacity.

While such a sophisticated system provides information about the entire pattern on the wafer, such information is often unnecessary. For example, many inspection or test procedures developed by the industry require only minimal point testing in unmasked areas. The exact location of the points to be tested is not particularly critical as long as the points are located in unmasked areas that are spaced out over the entire wafer. If the measured results of these tested points fall within the specified fabrication parameters, there is a reasonable probability that the manufacturing process has been properly carried out. In the latter approach, the test device would only need to be able to reliably locate unmasked areas on a semiconductor wafer, and the complex processing and storage requirements of a pattern recognition systems would be unnecessary.

Accordingly, it is an object of the subject invention to provide a new and improved method and apparatus for testing areas of interest on a workpiece where the areas of interest have an optical reflectivity different from the other areas on the workpiece.

It is a another object of the subject invention to provide an new and improved method and apparatus for identifying areas of interest on a workpiece for subsequent testing.

It is a further object of the subject invention to provide a new and improved method for identifying the unmasked areas on a semiconductor wafer.

It is another object of the subject invention to provide a new and improved method for identifying unmasked areas on a semiconductor wafer for subsequent testing.

It is a further object of the subject invention to provide a new and improved method for identifying unmasked areas on a semiconductor wafer which can then be tested for ion dopant concentrations.

It is still a further object of the subject invention to provide a new and improved apparatus for identify unmasked areas on a semiconductor wafer which can then be tested for the effects of processing steps such as etching procedures.

It is still another object of the subject invention to provide a new and improved apparatus which relies on the optical reflectivity of the surface of the sample to locate unmasked areas on a semiconductor wafer.

It is still a further object of the subject invention to provide a new and improved apparatus for identifying areas of interest on a workpiece utilizing a reflected search beam.

It is still another object of the subject invention to provide a new and improved apparatus wherein the search beam used for identifying the location of an area of interest on a workpiece, such as a semiconductor wafer, is subsequently used in the testing procedure.

SUMMARY OF THE INVENTION

In accordance with these and many other objects, the subject invention provides for a method and apparatus for testing areas of interest on a workpiece where the areas of interest have an optical reflectivity different from all of the other areas on a workpiece and where the location of the areas of interest are unknown. The method of the subject invention is performed by scanning the surface of the workpiece with a search beam and measuring the power of the reflected search beam as it is scanned. The reflected power of the search beam is a function of the optical reflectivity of the surface of the sample and therefore areas of interest can be identified by measuring the variations in power of the reflected beam. Once the areas of interest on the workpiece are identified, subsequent testing can be performed.

This broad method and apparatus can be put to particular use in the analysis of masked semiconductor wafers. Moreover, the subject invention may be used most conveniently in combination with methods and apparatus heretofore described using beams of radiation to test parameters in the sample. As will be seen below, one or more of the beams designed to perform a test measurement can be initially used as a search beam to locate the areas of interest to be tested.

In the preferred embodiment of the subject invention, the apparatus includes one laser for generating a pump beam of radiation. In addition, a second laser is provided for generating a probe beam of radiation. Either or both of these beams are initially used in a search and scanning mode for identifying unmasked areas on a semiconductor wafer. When these areas have been identified, a subsequent measurement can be made. In this subsequent measurement, the pump beam is intensity modulated and directed to the area of interest to be tested. The modulated pump beam periodically excites the surface of the sample. The probe beam is then directed within the periodically excited region on the surface of the sample. The modulations in the power of the reflected probe beam induced by the pump beam excitation are measured in order to evaluate the sample. The latter portion of the testing procedure is identical to that described in U.S. patent application Ser. No. 707,485, cited above. Other test procedures, such as the periodic deflection technique described in U.S. Pat. No. 4,521,118, cited above, could also be readily used, particularly in nonsemiconductor samples.

Further objects and advantages of the subject invention will become apparent from the following detailed description taken in conjunction with the drawings in which:

DETAILED DESCRIPTION OF THE PREFERRED EMBODIMENT

As noted above, the subject invention is intended to be utilized in any situation where the location of areas of interest to be tested are unknown and where those areas of interest have an optical reflectivity different from other areas on a workpiece. This situation could be encountered in the fabrication of the mask in a color television screen. This situation is also encountered in the fabrication of a semiconductor wafer. FIG. I is a simplified illustration of a semiconductor wafer during a fabrication step.

Figure 1:
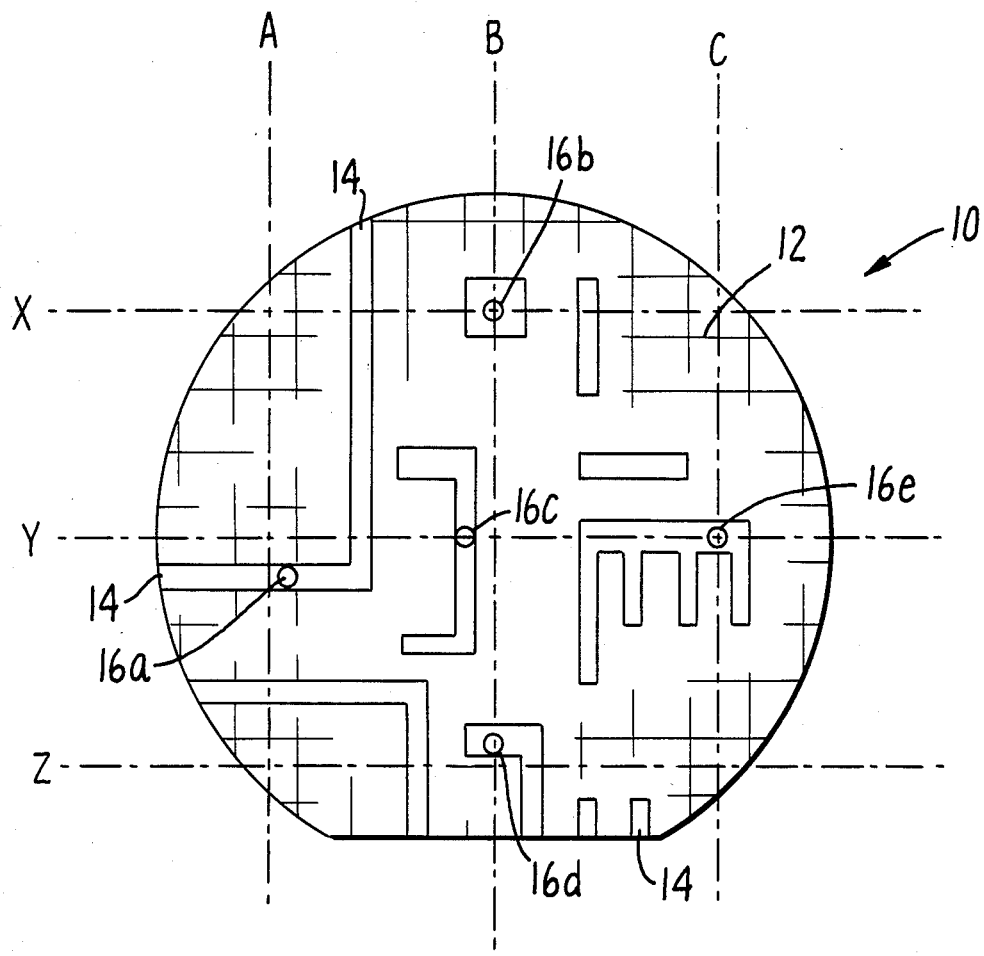
FIG. 1 is an illustration of masked semiconductor wafer depicting the concept of a 5-point test.

During the processing of semiconductors, the wafer 10 is coated with a photoresist material 12, typically an organic dye. A mask (not shown) is placed over the photoresist material and the wafer exposed to ultraviolet radiation. This step changes the character of the unmasked portions of the photoresist material so that they can then be removed in an etching step. The etching step will create a pattern of open areas 14 on the wafer as shown in FIG. 1. The patterned wafer is now subjected to other processes that etch, implant or deposit material into the unmasked regions of the wafer.

It is usually desirable and often necessary to inspect the wafer immediately after a processing step to determine if that step has been properly carried out. One standard inspection procedure in the industry is called a "5-point test." In this test, measurement equipment is moved to five locations (16a-e), each within an unmasked area on the wafer. These five locations, set out in a cross-like pattern, are spread out on the wafer in different regions. The exact location of each point is not critical since the information sought is intended to provide a reasonable assurance that the results of the fabrication step are within the desired parameters across the entire wafer. Since the exact location is not critical, a complex pattern recognition system is unnecessary. In fact, the five point test is typically carried out by a human operator using a microscope to direct the test probe. As will be seen below, the subject invention allows this search process to be automated with relatively simple hardware.

In the process of forming a semiconductor wafer, the unmasked areas are treated by various fabrication processes such as ion-doping. When the ion-doping process is completed, it is desirable to carry out a similar 5-point testing phase. The actual testing of the identified unmasked areas can be performed by a variety of devices. The subject invention will be described with reference to a particular testing system developed by the assignee of the subject invention.

Figure 2:
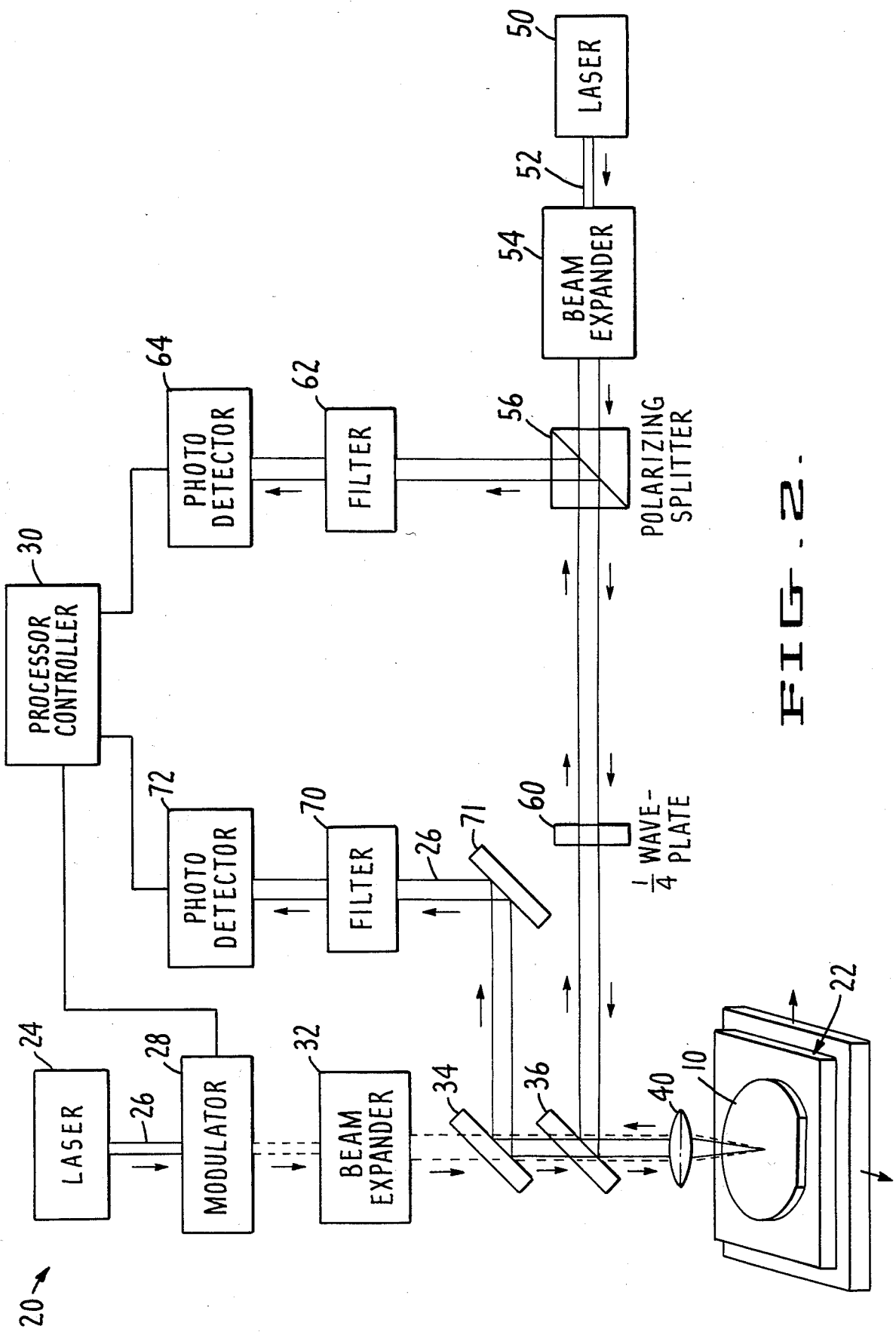
FIG. 2 is a block diagram of the apparatus for carrying out the method of the subject invention.

Turning now to FIG. 2, the preferred embodiment of the subject invention is illustrated. The device 20 includes standard X-Y stage system 22. The semiconductor wafer 10 is placed on the stage system enabling it to be scanned with reference to the radiation beams. The apparatus includes a first laser 24 generating a beam having energy sufficient to excite the electrons in a semiconductor above the band-gap energy. This excitation will create a photo-excited plasma which will directly affect the optical reflectivity of the surface of the wafer. A detailed explanation of this effect is described in the article cited above. The subject disclosure will focus primarily upon the modifications of such a system to permit the identification of unmasked areas on a semiconductor wafer.

Laser 24, which may be an argon-ion laser, generates a beam 26 that is passed through a modulator 28 which functions to intensity modulate the beam. The modulator 28 is controlled by a processor controller 30. As discussed below, when laser 24 functions as a search beam, the modulator need not be activated. Beam 26 is then passed through a beam expander 32 and is directed toward the wafer 10. Prior to impinging on the wafer, the beam passes through a glass plate 34 and a dichroic reflector 36 and is focused by a lens 40.

As illustrated in FIG. 2, the apparatus also includes a second laser 50 for generating a probe beam 52. Laser 50 is preferably a helium-neon laser. Beam 52 is passed through a beam expander 54 and a polarizing splitter 56. Beam 52 then passes through a quarter wave plate retarder 60 which functions to shift the phase or polarization state of the beam by 45 degrees. The beam is then reflected downwardly by dichroic mirror 36 and onto the workpiece. The coating on dichroic mirror 36 is designed to be essentially transparent to wavelengths generated by the argon laser and reflecting for the wavelengths generated by the helium-neon laser. Preferably, the probe beam 52 is focused coincident with the pump beam.

In the test procedure, the modulations in the power of the reflected probe beam are monitored to provide information about surface and near surface conditions in the semiconductor sample. The path of the reflected probe beam 52 includes a return to dichroic mirror 36 where it is reflected back through the quarter wave plate retarder 60. The retarder functions to shift the polarization of the beam another 45 degrees such that the polarization of the returning beam is a full 90 degrees out of phase from its original orientation. In this state, the polarizing splitter 56 will pick off the reflected probe beam and redirect that beam upwardly toward filter 62. Filter 62 is provided to block out any radiation from the pump beam 24. After passing through filter 62 the power of the probe beam is then measured by photodetector 64. Variations of the power of the probe beam can be used by the processor controller 30 to evaluate the characteristics of the semiconductor sample.

In accordance with the subject invention, either or both of the beams 26, 52 from the lasers can be used to locate the unmasked areas on the semiconductor. FIG. 2 illustrate the portions of the apparatus necessary to make these measurements. More specifically, glass plate 34 is provided to pick off a portion of the reflected pump beam. The glass plate 34 is intended to be essentially transparent. However, approximately four percent of the power of the pump beam reflected off the wafer will be picked off and directed toward filter 70 by plate 34. (A total reflector 71 is shown in the beam path between the glass plate 34 and filter 70 to simplify the layout of the schematic). Filter 70 is designed to remove any stray radiation from the probe beam prior to reaching photodetector 72. Photodetector 72 monitors the power of the reflected pump beam. When the pump laser is utilized as the search beam, the modulator need not be operated. As can be appreciated, because the optical reflectivity of the masked and unmasked areas on the wafer can be significantly different, the measurement of the power of the reflected beam can give an indication of the location of unmasked areas.

As noted above, the probe beam can also be used to identify the unmasked areas on the wafer. As illustrated in FIG. 2, the reflected probe beam is reflected by splitter 56, through filter 62 and onto photodetector 64. The power of the reflected probe beam is measured by photodetector 64.

As illustrated in FIG. 2, two photodetectors are utilized. Each photodetector is intended to provide a measure of the total power of a reflected beam of radiation. To achieve this result, the detectors are arranged such that the incoming beam will substantially underfill the surface of the detector. The reason that two different photodetectors/filter combinations are used is because the wavelengths of the beams are quite different. Accordingly, filters are selected to block the unwanted radiation from reaching the associated detector. The output of both the photodetectors is gated to the processor controller 30. In the actual apparatus, additional photodetectors (not shown) are employed to monitor the power of the laser beams as they are emitted from the lasers. These extra detectors are necessary so that the processor can compensate for unwanted fluctuations in the delivery power of the lasers.

Figure 3:
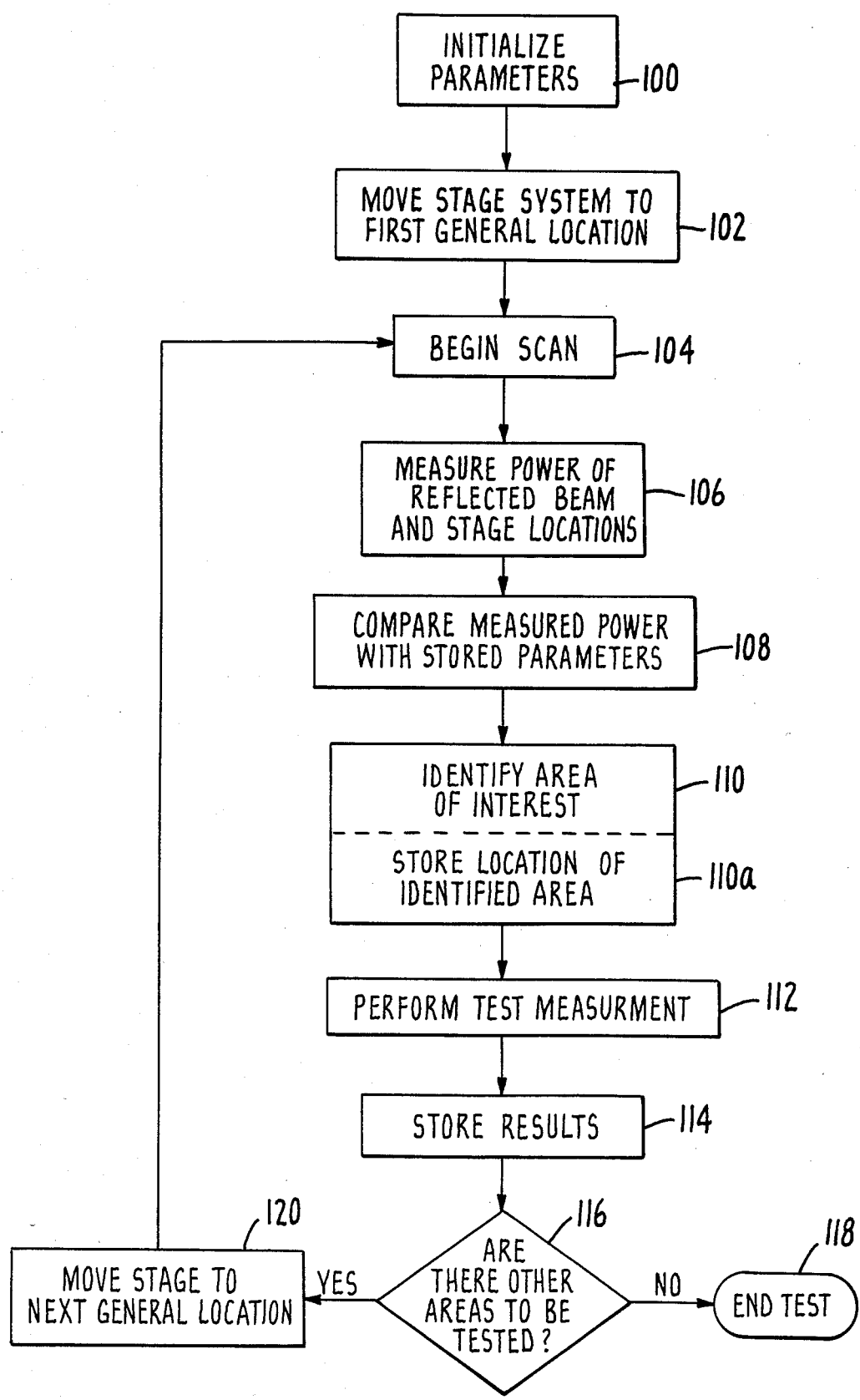
FIG. 3 is a flow chart illustrating high level instructions performed by the processor controller for carrying out the method of the subject invention.

Having described the apparatus of the subject invention, the method of practicing the invention will be described with reference to FIGS. 1 through 3. In this specific example, the apparatus 20 is programmed to perform a "5-point test" on a semiconductor wafer. It should be appreciated, however, that the software instructions controlling the processor can be arranged to perform many different types of testing procedures and the 5-point test is selected only by way of example.

At the start of the procedure, the parameters of the test sequence are initialized in step 100. Some of the parameters of the test sequence which may be programmed include the general location of the areas on the wafer to be scanned. In this case, five points must be located which more or less fall on the intersection of vertical lines A, B and C and horizontal lines X, Y and Z (shown in FIG. 1). These arbitrary intersections bear no relationship to the actual photoresist pattern formed on the wafer. Thus, the points defined by the intersection of the matrix lines will often be in areas that are coated with photoresist material rather than at an unmasked site. Preferably, the scanning system should be able to locate an area reasonably close to each point of intersection which is not coated with the photoresist material. When this area is located, the test procedure can be performed.

Another parameter which can be programmed during the initialization step is data representative of the optical reflectivity of the unmasked regions on the semiconductor which often have an oxide film coated on the silicon. This data can take the form of the actual expected optical reflectivity, programmed in terms of expected power of the reflected search beam. In the alternative, the program may be designed to accept the entry of the thickness of the oxide layer, if any is present, with the processor internally computing the expected power level of the search beam reflected from the unmasked regions.

A third parameter which can be programmed is the size of the areas of interest. More specifically, the focusing optics of the subject invention can provide a resolution in the 1-2 micron range. Thus, small gate regions on a semiconductor, which have the photoresist removed, can be identified as an area of interest. However, in certain test situations, it is desirable to take data only from areas that are significantly larger, such as scribe lines, which can have a width of approximately 100 microns. Thus, the initialization step can include a definition of the size of the area of interest to be tested.

Once the parameters are initialized, the stage system is then moved to the general region where the lines A and X intersect (step 102). The stage system is then moved to permit scanning of the lasers, in this general region, for a suitable unmasked location where a measurement can be made. (Step 104) The scan can either be in the X or Y direction using one or both of the laser beams as a search beam. The power of the reflected search beam along with the coordinates of the stage system are monitored in step 106. The measured power of the search beam is compared with the stored parameters in step 108. One or more areas suitable for measurement will be identified in this manner (step 110). Once an area of interest (for example, area 16a) has been identified, its location, as defined by the coordinates of the stage system, can be stored (step 110a) for future measurement. In the alternative, the area can be immediately tested as shown in step 112.

In the illustrated embodiment the test measurement will be performed by intensity modulating the pump beam 26 and measuring the periodic changes in the power of the reflected probe beam 52 induced by the pump beam. Information such as ion dopant concentrations or the effect of etching procedures can be obtained. The equipment illustrated in FIG. 2 could also detect thermal characteristics, using a beam deflection technique described in U.S. Pat. No. 4,521,118. The latter technique is particularly useful in non-semiconductor samples. These results are then stored in the processor at step 114.

The program will then determine whether there are any other areas to be tested in step 116. If all areas have been tested, the sequence will terminate at step 118. The tested wafer will be removed from the apparatus and a new wafer can then be loaded in its place. If, however, additional points are to be tested, the stage is moved to the next general location (such as 16b) as shown in step 120. The scanning procedure 104 can then begin again. This procedure is repeated until all five areas are located and tested.

This procedure can also be designed to complete the scan of the entire wafer before testing begins. In this manner, the best candidates for measurement sites can be identified prior to testing. When the stage is returned to the selected test site, a second, confirming search can be made to eliminate any accuracy problems, such as those induced by backlash, inherent in the mechanical movement of the stage system.

As mentioned above, one or both of the laser beams can be used as a search beam. In the case of a semiconductor wafer masked with a photoresist material, it has been found that using both laser beams is advantageous. More specifically, at any given wavelength, the reflectivity measured in a masked region can be close to that of an unmasked region. Where the reflectivity is similar, ambiguities can arise in identifying areas of interest. This ambiguity can be minimized when two quite different wavelengths are used, such as those from argon ion and helium neon lasers, since the optical characteristics of the photoresist material are very different at these two wavelengths.

In general, the greater the number of independent reflectivity measurements that are made at different wavelengths, the easier it becomes to specifically define the test conditions. Therefore, in practice, it is beneficial to scan and search with both the pump and probe beams and utilize whatever additional information is available to aid in identifying the areas of interest. It should also be understood that if the search beam is not generated from lasers already existing in the test hardware, then a wavelength should be selected for the search beam that provides the least ambiguous information for a given workpiece.

In summary, there has been provided a new and improved method and apparatus for identifying areas of interest on a workpiece which have an optical reflectivity different from all other areas on the workpiece. The method includes scanning the surface of the workpiece with a search beam. The reflected power of the search beam is a function of the optical reflectivity of the surface of the sample and is measured and processed to identify the location of the areas of interest on the sample. These areas of interest can then be tested. In the preferred embodiment, the areas of interest are the unmasked areas on a semiconductor wafer which are then evaluated to determine ion dopant concentrations or the effects of various processing steps such as etching.

While the subject invention has been described with reference to a preferred embodiment, other changes and variations could be made by one skilled in the art, without varying from the scope and spirit of the subject invention as defined by the appended claims.

We claim:

1. A method of testing an area of interest on a workpiece where the area of interest has an optical reflectivity different from all other areas on the workpiece and where the location of the area of interest is unknown, said method comprising the steps of:

scanning the surface of the workpiece with a pair of search beams in a manner such that said search beams are reflected, with each search beam having a different wavelength;

measuring the power of each of the reflected search beams as they are scanned;

processing the measured power of the reflected search beams to identify the location of the area of interest; and testing the identified area of interest.

2. A method as recited in claim I wherein at least one dimension of the area of interest to be tested must fall within a set parameter and further including the step of determining said dimension of the area of interest as the search beams are scanned over the workpiece.

3. A method of testing areas of interest on a workpiece where the areas of interest have an optical reflectivity different from all other areas on the workpiece and where the location of the areas of interest are unknown, said method comprising the steps of:

scanning the surface of the workpiece with a pair of search beams in a manner such that said search beams are reflected, with each search beam having a different wavelength;

measuring the power of each of the reflected search beams as they are scanned;

processing the measured power of the reflected search beams to identify the location of areas of interest;

storing the locations of the identified areas of interest; and selecting at least one of those identified areas for testing.

4. A method as recited in claim 3 wherein at least one dimension of the areas of interest to be tested must fall within a set parameter and further including the step of determining said dimension of the areas of interest as the search beams are scanned over the workpiece.

5. An apparatus for testing areas of interest on a workpiece where the areas of interest have an optical reflectivity different from all other areas on the workpiece and where the location of the areas of interest are unknown, said apparatus comprising:
   means for generating a first search beam of radiation, said first search beam having a first wavelength;
   means for generating a second search beam of radiation, said second search beam having a second wavelength different from said first wavelength;
   means for scanning said search beams over the surface of the workpiece such that they are reflected;
   means for measuring the power of the reflected search beams;
   processor means for identifying an area of interest on the workpiece based on the measured power of the reflected search beams; and
   means for testing the workpiece at the identified area of interest.

6. An apparatus as recited in claim 5 wherein said means for testing includes measuring the power of one of said beams of radiation with said measuring means.

7. An apparatus as recited in claim 5 wherein data representative of the optical reflectivity of the surface of the workpiece is stored in said processor means.

8. An apparatus as recited in claim 5 wherein said processor means stores the location of areas of interest that have been identified and selects certain of said identified areas for subsequent testing.

9. An apparatus as recited in claim 5 wherein the means for generating one of said beams is an argon ion laser.

10. An apparatus as recited in claim 5 wherein the means for generating one of said beams is a helium neon laser.

11. A method of evaluating surface conditions within the unmasked areas on a masked semiconductor wafer comprising the steps of:
   scanning the surface of the wafer with first and second search beams of radiation in a manner such that the beams are reflected, with each said beam having a different wavelength;
   measuring the power of the reflected search beams as they are scanned;
   processing the measured power of the reflected search beams to identify the location of unmasked areas on the wafer;
   periodically exciting the surface of the wafer within an identified unmasked area;
   directing said first beam of radiation within the region that is being periodically excited such that the first beam is reflected; and
   measuring the periodic reflected power of the first beam induced by the periodic excitation of the wafer to evaluate the surface conditions within the unmasked area.

12. A method as recited in claim 11 wherein said step of periodically exciting the surface of the wafer is performed by intensity modulating said second beam of radiation and directing said intensity modulated second beam of radiation onto the surface of the wafer.

13. A method as recited in claim 11 further including the step of storing the locations of the unmasked ares of interest that are identified and selecting at least one of those identified areas for subsequent evaluation.

14. A method as recited in claim 11 wherein at least one dimension of the unmasked areas to be tested must fall within a set parameter and further including the step of determining said dimension of the unmasked area as the search beam is scanned over the wafer.

15. An method as recited in claim 11 wherein the periodic variations in the reflected power of the first beam induced by the periodic excitation are used to evaluate ion dopant concentrations in the unmasked areas on the wafer.

16. An method as recited in claim 11 wherein the periodic variations in the reflected power of the first beam induced by the periodic excitation are used to evaluate effects of etching in the unmasked areas on the wafer.

17. An apparatus for evaluating surface conditions within the unmasked areas on a masked semiconductor wafer comprising:
   means for generating a pump beam of radiation having a first wavelength;
   means for intensity modulating the pump beam;
   means for generating a probe beam of radiation having a wavelength different from the pump beam;
   means for scanning said beams with respect to said wafer such that they are reflected;
   means for measuring the power of the reflected radiation beams; and
   processor means for controlling the operation of said beam generating means, modulating means, scanning means and measuring means, with both of said radiation beams being used as search beams that are scanned over the surface of the wafer, with the reflected power of the search beams being used to identify the location of unmasked areas on the wafer, and with selected ones of said identified areas being evaluated by intensity modulating and directing said pump beam onto an unmasked area and directing the probe beam into the region within that unmasked area that is being periodically excited by the pump beam, with the periodic changes in power of the reflected probe beam induced by the intensity modulated pump beam being used to evaluate the surface conditions on the wafer.

18. An apparatus as recited in claim 17 wherein data representative of the optical reflectivity of the surface of the wafer is stored in said processor means.

19. An apparatus as recited in claim 18 wherein said data corresponds to the oxide thickness on a semiconductor wafer and said processor means calculates the data representative of the optical reflectivity.

20. An apparatus as recited in claim 17 wherein the periodic changes in the reflected power of the probe beam induced by the modulated pump beam are used to evaluate ion dopant concentrations in the unmasked areas on the wafer.

21. An apparatus as recited in claim 17 wherein the periodic changes in the reflected power of the probe beam induced by the modulated pump beam are used to evaluate the effects of etching on the unmasked areas on the wafer.

22. An apparatus as recited in claim 17 wherein the means for generating said pump beam is an argon ion laser.

23. An apparatus as recited in claim 17 wherein the means for generating said probe beam is a helium nean laser.

* * * * *